(12) United States Patent
Blatchford

(10) Patent No.: US 6,241,775 B1
(45) Date of Patent: Jun. 5, 2001

(54) SPECIFICATION OF AN ARTIFICIAL LIMB

(75) Inventor: Brian Stephen Blatchford, Winchester (GB)

(73) Assignee: Chas. A. Blatchford & Sons Ltd. (GB)

( * ) Notice: Subject to any disclaimer, the term of this patent is extended or adjusted under 35 U.S.C. 154(b) by 0 days.

(21) Appl. No.: 09/318,175

(22) Filed: May 25, 1999

(51) Int. Cl.[7] .................................................. A61F 2/76
(52) U.S. Cl. ............................................. 623/27; 623/901
(58) Field of Search ............................... 623/27, 31–33, 623/36, 57, 58, 38, 901, 909; 700/103, 104

(56) References Cited

U.S. PATENT DOCUMENTS

| | | |
|---|---|---|
| 3,547,115 | 12/1970 | Stevens . |
| 5,225,987 | 7/1993 | Thompson ................. 364/468.09 |
| 5,442,563 | 8/1995 | Lee ............................ 364/468.1 |
| 5,800,565 | * 9/1998 | Biedermann ................... 623/38 |
| 5,825,651 | * 10/1998 | Gupta et al. .................. 700/103 |
| 5,972,035 | * 10/1999 | Blatchford ..................... 623/27 |

FOREIGN PATENT DOCUMENTS

| | | | |
|---|---|---|---|
| 0 163 121 A1 | 4/1985 | (EP) . | |
| 0 574 098 A1 | 1/1993 | (EP) . | |
| 0 801 936 A2 | * 10/1997 | (EP) | ........................ 623/27 |
| 8902888 | 6/1991 | (NL) | ........................ 623/901 |
| WO 94/18638 | 8/1994 | (WO) . | |

\* cited by examiner

*Primary Examiner*—David H. Willse
(74) *Attorney, Agent, or Firm*—Fish & Richardson P.C.

(57) ABSTRACT

A method of specifying the components of an artificial limb, includes the steps of:

providing at least one logical unit table arranged to contain data relating to a class of the components;

providing a plurality of component records located in the at least one logical unit table, in which each of the component records is arranged to hold data relating to a respective plurality of components of the same class, and in which at least one of the component records relates to a generic component;

providing for the at least one generic component record an associated set of specific component records and at least two option lists, each of which lists relates to a defined characteristic of the component of the associated generic component record;

in which the user selects an option from each list; and in which a unique specific component record is identified from the associated set thereof that is compatible with each selected option.

38 Claims, 2 Drawing Sheets

Microfiche Appendix Included
(1 Microfiche, 38 Pages)

SPECIFICATION OF AN ARTIFICIAL LIMB

BACKGROUND OF THE INVENTION

A microfiche appendix containing Pascal language source code for specifying the components of an artificial limb consisting of 38 microfiche images on one microfiche card is filed herewith. A portion of the disclosure of the patent document is subject to copyright protection. The copyright owners have no objection to the facsimile reproduction by anyone of the patent document or the patent disclosure, as it appears in the Patent & Trademark Office patent file or records, but otherwise reserves all copyright rights whatsoever.

The present invention relates to a method of specifying the components of an artificial limb, a method of constructing such an artificial limb, and to apparatus for specifying the components.

An artificial limb comprises many components which must fit together correctly to ensure correct functioning of the limb. Components for a complete limb can be sourced from one or more manufacturers. In many cases, one manufacturer's product range can cover a diverse range of options and can be used with another manufacturer's products in the construction of a single limb. Thus, it can be a complicated and skilled job to select components which permit a limb to perform the required functions and which fit correctly together. Furthermore it is difficult accurately to estimate the cost of a complete limb prior to construction since errors in its specification may not be realised until construction is attempted.

SUMMARY OF THE INVENTION

It is an object of the present invention to provide an improved method and means of specifying the components which make up an artificial limb.

According to a first aspect of the present invention, there is provided a method of specifying the components of an artificial limb, comprising the steps of providing at least one logical unit table arranged to contain data relating to a class of the components; providing a plurality of component records located in said at least one logical unit table, in which each of said component records is arranged to hold data relating to a respective plurality of components of the same class, and in which at least one of said component records relates to a generic component; providing for said at least one generic component record an associated set of specific component records and at least two option lists, each of which lists relates to a defined characteristic of the component of the associated generic component record; in which the user selects an option from each list; and in which a unique specific component record is identified from said associated set thereof that is compatible with each selected option.

An artificial limb may be constructed from individual components associated with component records as specified in accordance with the first said aspect of the invention.

In accordance with a second aspect of the present invention, there is provided a method of specifying the components of an artificial limb, comprising the steps of providing a plurality of logical unit tables arranged to contain data relating to respective classes of the components; providing a plurality of component records located in at least one of the logical unit tables, in which each of said component records is arranged to hold data relating to a respective plurality of components of the same class, and in which at least one of said component records relates to a generic component; providing for said at least one generic component record an associated set of specific component records and at least two option lists, each of which lists relates to a defined characteristic of the component of the associated generic component record; in which the user selects an option from each list; and in which a unique specific component record is identified from said associated set thereof that is compatible with each selected option; providing an interface field for each respective component record, said interface fields being arranged to hold data relating to an interface of the component to which the respective component record relates; and generating a list of compatible component records from at least one logical unit table other than the logical unit table containing the said identified specific component record, the said compatible component records being compatible with the said identified specific component record taking account of the data held in the interface fields of the said identified specific component record and the component records in said other logical unit table.

An artificial limb may be constructed from individual components associated with component records as specified in accordance with the second aspect of the invention, to include the specific component to which the or each identified specific component record relates and at least one component to which a compatible component record relates.

A plurality of sets of selectable option lists may advantageously be provided for the or each generic component record, and a specific component record may be identified from each of said sets.

It may be arranged that the specific component record or records available for selection in one or more of the sets of selectable option lists is dependent upon which specific component record has already been identified from one or more other of said sets of selectable option lists or other component record.

It is to be understood that more than one of the component records may relate to a respective generic component. Accordingly, option lists and specific component records, and their associated specific components, may be available for each generic component record.

In this way, where a component record generically relates to a general description of a component, one or more subsets thereof can be specifically identified. A subset may, for example, relate to a specific size, or a specific manufacturer, or a specific material, or a left-or-right-sided component. The selection procedure may involve the user being presented with a set of options, specific components, for selection, or being asked questions, the answers to which are used in the determination of the specific component. It will be appreciated that identification selection of one specific component may effect, for example restrict, the range of other components that are compatible therewith. Accordingly, the selection procedure may respond to the selection of a specific component by varying the selection available for specifying in respect of an associated component of the limb.

The classes of components in an above-knee prosthesis will typically be a socket, an alignment mechanism, a shin/knee component, an ankle component, a foot and a cosmesis. Once a component record has been selected, which might for example be from the logical unit related to the shin component class, a list of compatible component records relating to the class of ankle components may be generated. Since the information held in the interface fields relating to the particular shin component has been taken into account when generating the list, the list will only include component records relating to ankle components which can be connected to the chosen shin component. For other amputation levels different classes of component may be selected.

Preferably a further component record is selected from the generated list and a further list of compatible component records is generated based on the further component record. This may for example be a list of feet that can be connected to the chosen ankle component. By repeating this process, to select a component from each class i.e. from each logical unit table, a complete limb may be specified and then constructed in accordance with the present invention.

Preferably the method includes selecting a further component record from the first list, generating a further list of compatible component records based on the further component record and repeating the selection and list generation steps until the required number of components have been specified.

Typically the method includes providing an interface table and further includes arranging each interface field to include a pointer to the interface table. Advantageously, the interface table may include details of any components which may be required to adapt a component to fit to another component so that the generated list may also include a list of components associated with the components related to the listed component records. In this way, a user of the invention, may be provided with a complete parts list for the limb including any additional components which fall outside the classes of components selected for entry into the logical unit tables. This is particularly advantageous since the selection of appropriate adaptors is a particularly skilled task.

In accordance with a third aspect of the invention, there is provided apparatus for specifying the components of an artificial limb, comprising: a plurality of logical unit tables arranged to contain data relating to a respective class of the components; a plurality of component records located in at least one of the logical unit tables arranged to hold data relating to a respective plurality of components of the same class, in which at least one of said component records relates to a generic component; or said at least one generic component record, an associated set of specific component records and at least two option lists, each of which lists relates to a defined character of the component of the associated generic component record; and means for identifying a unique specific component record from said associated set thereof that is compatible with each of said selected options.

In accordance with a fourth aspect of the invention there is provided apparatus for specifying the component of an artificial limb comprising: a plurality of logical unit tables arranged to contain data relating to a respective class of the components: a plurality of component records located in a least one of the logical unit tables arranged to hold data relating to a respective plurality of components of the same class at least one of said component records being arranged to relate to a generic component; for said at least one generic component record, an associated set of specific component records and at least two option lists, each of which lists relates to a defined characteristic of the component of the associated generic component record; an interface field located in each respective component record arranged to hold data relating to an interface of the component to which the component record relates; user input means for selecting an option from each of said option lists; means for identifying from said associated set of specific component records a unique specific component record that is compatible with each selected option; and output means for outputting a list of compatible component records from a logical unit table other than the logical unit table containing the identified specific component record, which are compatible with the identified specific component record taking account of the data contained in the interface fields of the said identified component record and the component records in the other logical unit table.

Preferably, the apparatus of the invention is implemented by means of a computer system that stores the logical unit tables, computer records, option lists and interface fields, as appropriate, and a computer program to enable the method of the invention to be carried out. For example, the component records may be arranged to be displayed on a monitor of the system, and selecting a displayed generic component record may be arranged to display the option lists associated therewith.

In yet another aspect of the invention, a computer program for specifying the components of an artificial limb, residing on a computer-readable medium, includes instructions for causing a computer to: provide at least one logical unit table arranged to obtain data relating to a class of the components; provide a plurality of component records located in said at least one logical unit table, in which each of the component records is arranged to hold data relating to a respective plurality of components of the same class, and in which at least one of the component records is a generic component record relating to a generic component; provide for the at least one generic component record an associated set of specific component records and at least two option lists, each of which option lists relates to a defined characteristic of the generic component of the associated generic component record; allow a user to select an option from each option list; and identify a unique specific component record from the associated set of specific component records thereof that is compatible with each selected option.

In still another aspect, the invention provides a computer program for specifying the components of an artificial limb, residing on a computer-readable medium, including instructions for causing a computer to: provide a plurality of logical unit tables arranged to contain data relating to respective classes of the components; provide a plurality of component records located in at least one of the logical unit tables, in which each of the component records is arranged to hold data relating to a respective plurality of components of the same class, and in which at least one of the component records is a generic component record relating to a generic component; provide for the at least one generic component record an associated set of specific component records and at least two option lists, each of which option lists relates to a defined characteristic of the generic component of the associated generic component record; allow a user to select an option from each option list; identify a unique specific component record from the associated set thereof that is compatible with each selected option; provide an interface field for each respective component record, said interface fields being arranged to hold data relating to an interface of the component to which the respective component record relates; and generate a list of compatible component records from at least one logical unit table other than the logical unit table containing said identified specific component record, the compatible records being compatible with the identified specific component record taking account of the data held in the interface fields of the identified specific component record and the component records in the other logical unit table.

The invention further provides an article of manufacture, which includes a computer usable medium having computer readable program code embodied therein for specifying the components of an artificial limb. The article includes computer readable program code for causing the computer to: provide at least one logical unit table arranged to contain data relating to a class of the components; provide a plurality of component records located in said at least one logical unit table, in which each of said component records is arranged to hold data relating to a respective plurality of components of the same class, and in which at least one of said component records is a generic component record relating to a generic component; provide for said at least one generic component record an associated set of specific component records and at least two option lists, each of which option lists relates to a defined characteristic of the generic component of the associated generic component record; allow a user to select an option from each option list; and identify a unique specific component record from said associated set of specific component records thereof that is compatible with each selected option.

In yet another aspect, the article includes computer readable program code for causing the computer to: provide a plurality of logical unit tables arranged to contain data relating to respective classes of the components; provide a plurality of component records located in at least one of the logical unit tables, in which each of said component records is arranged to hold data relating to a respective plurality of components of the same class, and in which at least one of the component records is a generic component record relating to a generic component; provide for said at least one generic component record an associated set of specific component records and at least two option lists, each of which option lists relates to a defined characteristic of the generic component of the associated generic component record; allow a user to select an option from each option list; identify a unique specific component record from the associated set thereof that is compatible with each selected option; provide an interface field for each respective component record, the interface fields being arranged to hold data relating to an interface of the component to which the respective component record relates; and generate a list of compatible component records from at least one logical unit table other than the logical unit table containing the identified specific component record, the compatible records being compatible with the identified specific component record taking account of the data held in the interface fields of the identified specific component record and the component records in the other logical unit table.

Typically a component such as a shin/knee component will have three interface tables associated with it, one for its upper interface for example with an alignment mechanism, one for its lower interface for example with an ankle component, and one between the shin/knee and a cosmesis. The table relating to the interface between the ankle and the shin is preferably a single table which is pointed to by the interface fields of both the shin/knee logical unit table and the ankle logical unit table.

BRIEF DESCRIPTION OF THE DRAWING

The invention will now be described by way of example with reference to.

DETAILED DESCRIPTION OF THE INVENTION

Figure 1:
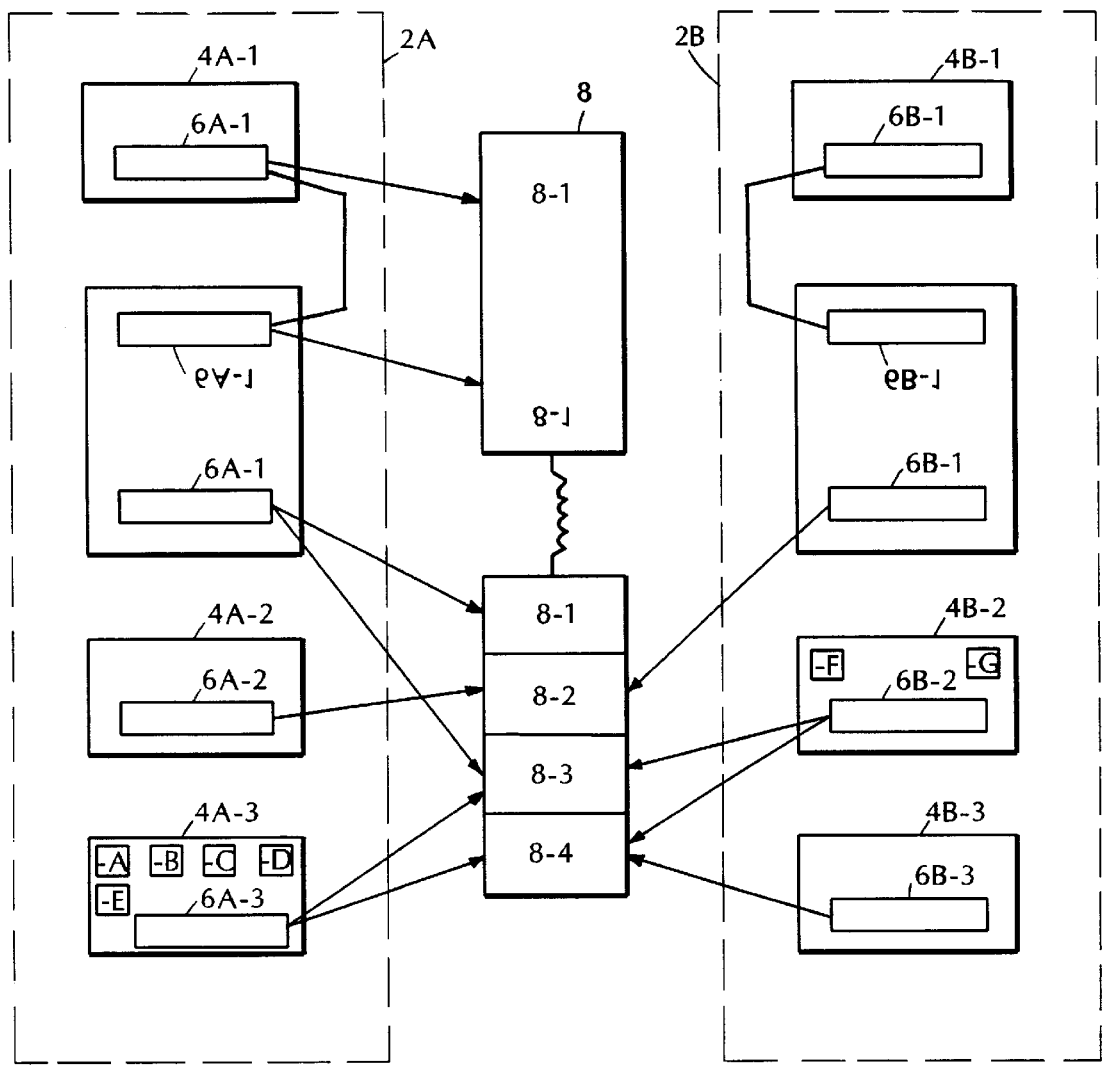
FIG. 1 which is a schematic block diagram of an apparatus constructed in accordance with the invention.

With reference to FIG. 1, logical unit tables 2A, 2B hold respective component records 4A-1, 4A-2, 4A-3, 4B-1, 4B-2, 4B-3 which in turn each hold interface fields 6A-1, to 6B-3. Each interface field contains a pointer to at least one entry in an interface table 8.

Each logical unit table 2 contains components records 4 relating to a particular respective class of components of a limb, for example a foot component and an ankle component. Each component record 4 represents a particular example of that class of component perhaps from a different product range of the same manufacturer or from a different manufacturer.

The interface table 8 contains in each entry, information relating to each possible physical interconnection or interface between the two classes of components. Where a class of component has more than one interface for example a knee/shin component which must interconnect with an alignment mechanism at its upper interface and with an ankle component at its lower interface, a separate interface table is provided for each physical interface.

Each entry in the interface table represents a different type of interconnection between components.

Taking component record 4A-1 as an example, it will be seen that its interface field 6A-1 points to two entries in the table 8, namely entries 8-1 and 8-3. This component record therefore relates to a component having two possible methods of interconnection with a component of the class represented by logical unit 2B. Looking at logical unit 2B however it is clear that no component records of this class of components point to interface table entry 8-1. Thus there are not components of the class represented by logical unit 2B which can be interconnected using the interface type represented by interface table entry 8-1 to connect with the component represented by component record 4A-1. From the diagram it is clear that the only component which can be used with the component represented by component record 4A-1 is the component represented by component record 4B-2, since these may be interconnected using this interface type represented by interface table entry 8-3.

In some circumstances it will be necessary to fit adaptor kits to components to allow them to connect to other components. In this case the corresponding entry in interface table 8 contains details of the necessary adaptor kit. If the table contains a null entry then the two components may be fitted directly together.

Once one of the components has been selected by a user from a logical unit table, for example component record 4A-3, the apparatus in accordance with the invention generates a list of possible component records which may be chosen from the logical unit table 2B. In this example the list will include the components represented by component records 4B-2 (via the interfaces represented either by interface table entry 8-3 or 8-4) and the component represented by component record 4B-3. Since for component 4B-2 there is a choice of interface methods it is likely that one of these will involve the use of an adaptor kit. In this case then the list will include three entries, two of the component represented by component record 4B-2 (one including an adaptor kit) and an entry relating to the component represented by component record 4B-3. Similarly the component represented by the selected component record has two possible interfaces (entries 8-3 and 8-4) one of which also is likely to involve the use of an adaptor kit.

The user having been presented with the list of components which may be connected to the first selected component, may select one of these listed components to generate a further list of components. For example having selected a shin and been presented with a list of possible ankles, the user may then select one of the ankles to determine which feet may be connected to that ankle. In this way a complete list of components to specify a whole limb may be produced.

One or more of the component records 4 may relate to a generic component, and the apparatus is then provided with a plurality of one or more specific component records associated with each generic component record, whereby the particular component to be specified for the limb is to be uniquely defined. By way of example, the component record 4A-3 of logical unit 2A relates to a particular range of prosthetic feet from a particular manufacturer, and is shown as being a generic record with mappings to two specific sets of component record -A and -B relating respectively to the foot size and foot side that the associated specific components have. Each generic component record has at least one such mapping which is unique to that generic component record. When all the generic component records are identified in a limb build including in this example component record 4A-3, the system identifies all the mappings that are needed to replace each generic component record by its required specific component record. Each mapping consist of a list of options that the user can choose, and each option corresponds to a set of specific component records that are appropriate for each generic component record covered by this mapping. For his example, mapping -A gives a set of feet for each size (e.g. size 22 to size 30) that the user can select, and mapping -B gives a set of feet for each amputation side (left or right) that the user can select. When the user has selected the required option from such set that is presented for that particular generic component, the program uses this information further to define the relevant component. To get the actual specific component record that satisfies the user requirements, the system will take the intersection of the two sets given by the options selected for the size of foot and amputation side with the set of all the specific component records that are compatible with that generic component. These mappings can also affect other component records. For example the generic component record for the ankle fairing will also be dependent on the foot size, and thus will also use mapping -B; the intersection with the set of all ankle fairing records will ensure that a specific ankle fairing record is selected rather than a specific foot record. Other generic component records can need more mappings; e.g. to translate a record of a Multiflex Ankle generic component record to a specific component record, the system will need three mappings, namely -C which deals whether it is a standard or lightweight ankle, -D which deals with the ankle ball hardness and -E which deals with the ankle snubber hardness. On completion of the selection and subsequent mapping, the program stored in the computer will then replace the given generic component record with the now uniquely specified component record, relating to the foot for example, to be employed in the artificial limb.

Having made this unique specification from record 4A-3, the computer program will consider whether there are any specific records, such as -F, -G in the associated compatible generic component record 4B-2, for example, of logic unit 2B that are to be excluded from presentation to the user on the basis that they are not specifically compatible and thus are not available for selection therewith.

Conceptually, each logical unit (comprising a class of components and its associated interface information) maps onto one or more components which perform the function required of a particular logical unit (e.g. a foot or ankle). A plurality of components may be required for a complete logical unit where an interface or adaptor kit is required. In some cases, the interface may be integral with the component. In this case, the component record will reflect a choice of component (chosen to select the appropriate interface). Thus, the underlying part number for a component may change according to interface requirements.

Figure 2:
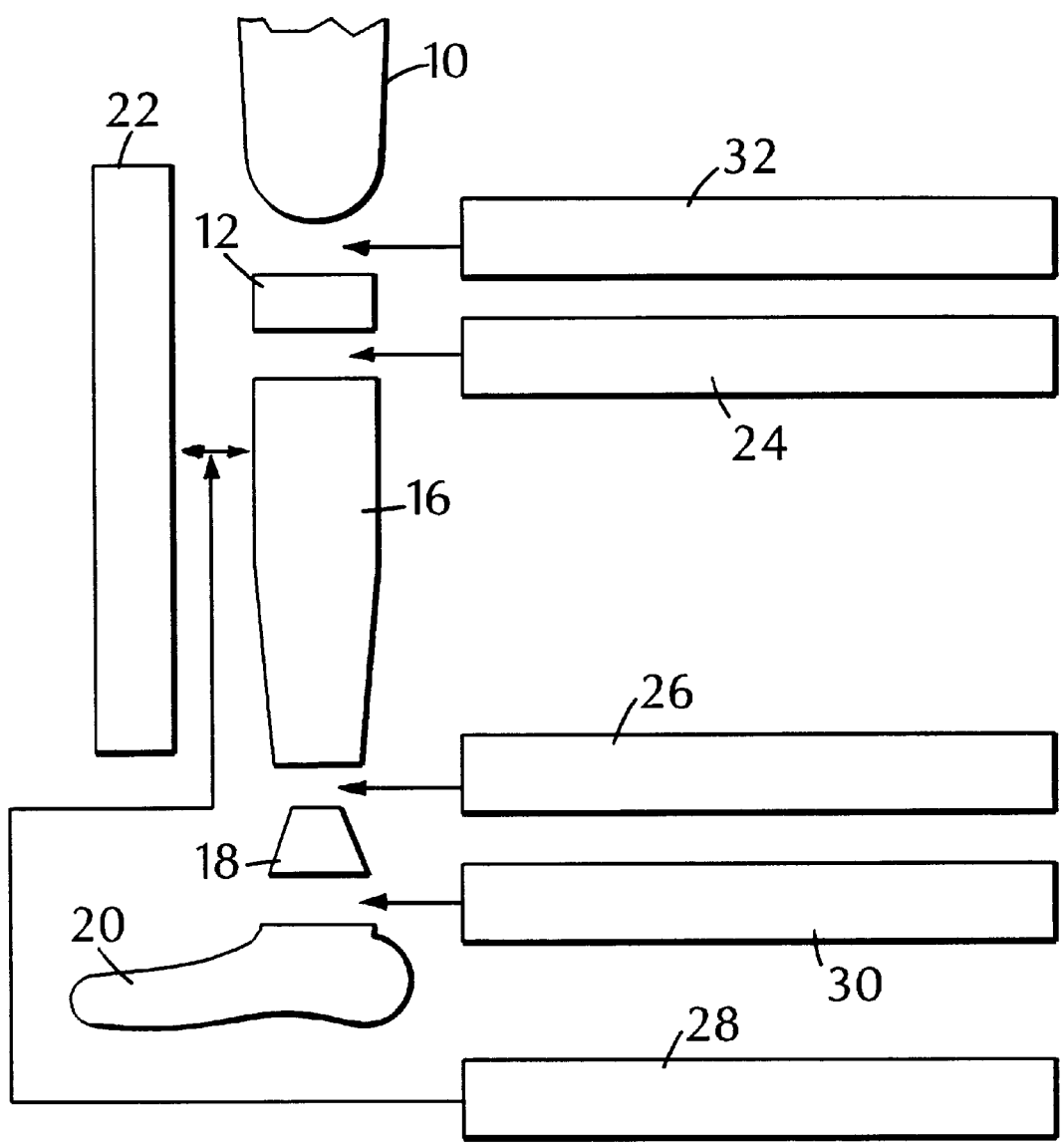
FIG. 2 which is a schematic diagram of the logical units of an above-knee prosthesis showing interface tables in accordance with the invention.

The division of an above knee prosthesis into several logical units each having a logical unit database is shown in FIG. 2.

The prosthesis is divided into six logical units namely a socket 10, an alignment mechanism 12, a shin/knee component 16, an ankle component 18, a foot component 20 and a cosmesis 22. Information about each possible component for each logical unit is held in a separate information table which in particular may hold a price, a part number, a maximum weight limit, approval information, the name of the manufacturer and a common name of the component which will be recognized by the user. Since a component may be included in several component records, storage space is saved by storing the detailed information of the information table, once only for a particular component.

Taking as an example, the shin/knee 16, this has three interfaces represented by tables 24, 26, and 28. These are the tables number 8 in FIG. 1. Thus a component record for a shin/knee component will have pointers to three interface tables since a knee component has three interfaces, namely those with the alignment mechanism, the ankle, and the cosmesis.

The model described above sometimes must be varied to accommodate peculiarities in the product ranges provided by manufacturers. For example, the fixings of the knee/shin component may vary depending on whether a continuous or discontinuous cosmesis is used. In this case, the interface table holds two entries which are both presented as options in the output list. The two entries relate to the components which must be used to interconnect the shin/knee component depending on which type of cosmesis is to be used. Similarly, in certain product ranges, there is no interface between the ankle and shin components since the shin component connects directly between the foot and the alignment mechanism and includes an ankle component. In this case, the interface field for that shin/knee component record points directly to entries in the ankle-foot interface table 30 which entries will in turn, be pointed to by interface fields from compatible feet. Also shown in FIG. 2 is an interface table 32 between the socket 10 and the alignment mechanism 12.

In summary, the invention provides a tool which greatly simplifies the selection of appropriate components for the construction of an artificial limb by presenting a user with a list of compatible components by taking account of the characteristics of each component. The list is refined by the user making selections from a presented list in order to cause the generation of one or more further lists.

The described techniques and mechanisms are not limited to any particular hardware or software configuration, but rather they may find applicability in any computing environment in which prosthesis designers operate. These technique and mechanisms may be implemented in hardware or software, or a combination of the two. Preferably, implementation is achieved with computer programs executing on programmable computes that each include a processor, a storage medium readable by the processor (including volatile and non-volatile memory and/or storage elements), and suitable input and output devices. Program code is applied to data entered using the input device to perform the functions described and to generate output information. The output information is applied to one or more output devices. Each computer program is preferably stored on a storage medium or device (e.g., CD-ROM, hard disk, or magnetic diskette) that is readable by a general or special purpose programmable computer for configuring and operating the computer when the storage medium or device is read by the computer to perform the procedures described in this document. The system may also be implemented as a computer-readable storage medium, configured with a computer program, where the storage medium so configured causes a computer to operate in a specific and predefined manner.

Other embodiments are within the scope of the following claims.

What is claimed is:

1. A method of specifying the components of an artificial limb, comprising the steps of:

providing at least one logical unit table arranged to contain data relating to a class of the components;

providing a plurality of component records located in said at least one logical unit table, in which each of said component records is arranged to hold data relating to a respective plurality of components of the same class, and in which at least one of said component records relates to a generic component;

providing for said at least one generic component record as associated set of specific component records and at least two option lists, each of which lists relates to a defined characteristic of the component of the associated generic component record;

in which the user selects an option from each list; and in which a unique specific component record is identified from said associated set thereof that is compatible with each selected option.

2. A method as claimed in claim 1, in which each option of the option lists comprises a further set of specific component records; and in which the unique specific component record is identified by forming the intersection of the further specific component records of the selected options and the said associated set of specific component records.

3. A method as claimed in claim 1, in which at least one of said option lists is made available to the user for selection therefrom in at least two of said generic component records.

4. A method as claimed in claim 1, in which each of a plurality of said component records relates to a respective generic component.

5. A method according to claim 4, in which for each of said generic component records there is provided a respective associated set of specific component records and at least two option lists.

6. A method of constructing an artificial limb from individual components, in which said components are specified in accordance with claim 1, and in which the artificial limb is constructed to include a specific component associated with the said identified specific component record.

7. A method of specifying the components of an artificial limb, comprising the steps of:

providing a plurality of logical unit tables arranged to contain data relating to respective classes of the component;

providing a plurality of component records located in at least one of the logical unit tables, in which each of said component records is arranged to hold data relating to a respective plurality of components of the same class, and in which at least one of said component records relates to a generic component;

providing for said at least one generic component record an associated set of specific component records and at least two option lists, each of which lists relates to a defined characteristic of the component of the associated generic component record;

in which the user selects an option from each list; and in which a unique specific component record is identified from said associated set thereof that is compatible with each selected option;

providing an interface field for each respective component record, said interface fields being arranged to hold data relating to an interface of the component to which the respective component record relates; and generating a list of compatible component records from at least one logical unit table other than the logical unit table containing the said identified specific component record, the said compatible component records being compatible with the said identified specific component record taking account of the data held in the interface fields of the said identified specific component record and the component records in said other logical unit table.

8. A method as claimed in claim 7, in which each option of the option lists comprises a further set of specific component records; and in which the unique specific component record is identified by forming the intersection of the further specific component records of the selected options and the said associated set of specific component records.

9. A method as claimed in claim 7 in which at least one of said option lists is made available to the user for selection therefrom in at least two of said generic component records.

10. A method as claimed in claim 7, in which each one of a plurality of said component records relates to a respective generic component.

11. A method as claimed in claim 10, in which for each of said generic component records there is provided a respective associated set of specific component records and at least two option lists.

12. A method of constructing an artificial limb from a plurality of components, in which the components are specified in accordance with claim 7, and in which the artificial limb is constructed to include (a) the specific component to which the said identified specific component record relates and (b) at least one component to which one of the compatible component records relates.

13. A method as claimed in claim 7, in which at least one of said compatible component records relates to a further generic component, the method further comprising:

providing for said at least one further generic component record an associated set of further specific component records and at least two option lists, each of which lists relates to a defined characteristic of the component of the associated further generic component record;

in which the user selects an option from each list; and in which a unique further specific component record is identified from said further associated set thereof that is compatible with each selected option.

14. Apparatus for specifying the components of an artificial limb, comprising:

a plurality of logical unit tables arranged to contain data relating to a respective class of the components;

a plurality of component records located in at least one of the logical unit tables arranged to hold data relating to a respective plurality of components of the same class, in which at least one of said component records relates to a generic component;

for said least one generic component record, an associated set of specific component records and at least two option lists, each of which lists relates to a defined character of the component of the associated generic component record; and a processor programmed to identify a unique specific component record from said associated set thereof that is compatible with each of said selected options.

15. Apparatus as claimed in claim 14, in which each option of the option lists comprises a further set of specific component records, and in which said processor is arranged to identify said unique specific component records by forming the intersection of the said further specific component records and the associated set of specific component records.

16. Apparatus for specifying the components of an artificial limb comprising:

a plurality of logical unit tables arranged to contain data relating to a respective class of the components:

a plurality of component records located in at least one of the logical unit tables arranged to hold data relating to a respective plurality of components of the same class at least one of said component records being arranged to relate to a generic component;

for said at least one generic component record, an associated set of specific component records and at least two option lists, each of which lists relates to a defined characteristic of the component of the associated generic component record;

an interface field located in each respective component record arranged to hold data relating to an interface of the component to which the component record relates;

a user interface allowing the user to select an option from each of said option lists;

a processor programmed to identify from said associated set of specific component records a unique specific component record that is compatible with each selected option; and an output for outputting a list of compatible component records from a logical unit table other than the logical unit table containing the identified specific component record, which are compatible with the identified specific component record taking account of the data contained in the interface fields of the said identified component record and the component records in the other logical unit table.

17. A computer program for specifying the components of an artificial limb, residing on a computer-readable medium, comprising instructions for causing a computer to:

provide at least one logical unit table arranged to contain data relating to a class of the components;

provide a plurality of component records located in said at least one logical unit table, in which each of said component records is arranged to hold data relating to a respective plurality of components of the same class, and in which at least one of said component records is a generic component record relating to a generic component;

provide for said at least one generic component record an associated set of specific component records and at least two option lists, each of which option lists relates to a defined characteristic of the generic component of the associated generic component record;

allow a user to select an option from each option list; and identifying a unique specific component record from said associated set of specific component records thereof that is compatible with each selected option.

18. The computer program of claim 17, wherein each option of the option lists comprises a further set of specific component records; and wherein the instructions for causing the computer to identify the unique specific component record includes instructions for causing the computer to form the intersection of the further specific component records of the selected options and said associated set of specific component records.

19. The computer program of claim 17, further comprising instructions causing the computer to make at least one of said options lists available to the user for selection therefrom in at least two of said generic component records.

20. The computer program of claim 17, wherein each of a plurality of said component records is a generic component record relating to a respective generic component.

21. The computer program of claim 20, further comprising instructions for causing the computer to provide for each of said generic component records a respective associated set of specific component records and at least two option lists.

22. A computer program for specifying the components of an artificial limb, residing on a computer-readable medium, comprising instructions for causing a computer to:

provide a plurality of logical unit tables arranged to contain data relating to respective classes of the components;

provide a plurality of component records located in at least one of the logical unit tables, in which each of said component records is arranged to hold data relating to a respective plurality of components of the same class, and in which at least one of said component records is a generic component record relating to a generic component;

provide for said at least one generic component record an associated set of specific component records and at least two option lists, each of which lists relates to a defined characteristic of the generic component of the associated generic component record;

allow a user to select an option from each list;

identify a unique specific component record from said associated set thereof that is compatible with each selected option;

provide an interface field for each respective component record, said interface fields being arranged to hold data relating to an interface of the component to which the respective component record relates; and generate a list of compatible component records from at least one logical unit table other than the logical unit table containing said identified specific component record, said compatible records being compatible with said identified specific component record taking account of the data held in the interface fields of said identified specific component record and the component records in said other logical unit table.

23. The computer program of claim 22, wherein each option of the option lists comprises a further set of specific component records; and wherein the instructions for causing the computer to identify the unique specific component record includes instructions for causing the computer to form the intersection of the further specific component records of the selected options and the associated set of specific component records.

24. The computer program of claim 22, further comprising instructions causing the computer to make at least one of said option lists available to the user for selection therefrom in at least two of said generic component records.

25. The computer program of claim 22, wherein each one of a plurality of said component records is a generic component record relating to a respective generic component.

26. The computer program of claim 25, further comprising instructions for causing the computer to provide for each of said generic component records a respective associated set of specific component records and at least two option lists.

27. The computer program of claim 22, wherein at least one of said compatible component records is a further generic component record relating to a further generic component, and wherein the instructions further cause the computer to:
provide for said at least one further generic component record an associated set of further specific component records and at least two option lists, each of which option lists relates to a defined characteristic of the component of the associated further generic component record;
allow the user to select an option from each option list associated with the further generic component record; and
identify a unique further specific component record from said further associated set thereof that is compatible with each option selected from the option lists associated with the further generic component record.

28. An article of manufacture, comprising:
a computer usable medium having computer readable program code embodied therein for specifying the components of an artificial limb, including computer readable program code for causing the computer to:
provide at least one logical unit table arranged to contain data relating to a class of the components;
provide a plurality of component records located in said at least one logical unit table, in which each of said component records is arranged to hold data relating to a respective plurality of components of the same class, and in which at least one of said component record is a generic component record relating to a generic component;
provide for said at least one genetic component record an associated set of specific component records and at least two option lists, each of which option lists relates to a defined characteristic of the generic component of the associated generic component record;
allow a user to select an option from each option list; and
identify a unique specific component record from said associated set of specific component records thereof that is compatible with each selected option.

29. The article of manufacture of claim 28, wherein each option of the option lists comprises a further set of specific component records; and wherein the program code for causing the computer to identify the unique specific component record includes program code for causing the computer to form the intersection of the further specific component records of the selected option and said associated set of specific component records.

30. The article of manufacture of claim 28, wherein the program code further causes the computer to make at least one of said options lists available to the user for selection therefrom in at least two of said generic component records.

31. The article of manufacture of claim 28, wherein each of the plurality of said computer records is a generic component record relating to a respective generic component.

32. The article of manufacture of claim 31, further comprising program code for causing the computer to provide for each of said generic component records a respective associated set of specific component records and at least two option lists.

33. A article of manufacture, comprising:
a computer usable medium having computer readable program code embodied therein for specifying the components of an artificial limb, including computer readable program code for causing the computer to:
provide a plurality of logical unit tables arranged to contain data relating to respective classes of the components;
provide a plurality of component records located in at least one of the logical unit tables, in which each of said component records is arranged to hold data relating to a respective plurality of components of the same class, and in which at least one of said component records is a generic component record relating to a generic component;
provide for said at least one generic component record an associated set of specific component records and at least two option lists, each of which lists relates to a defined characteristic of the generic component of the associated generic component record;
allow a user to select an option from each list;
identify a unique specific component record from said associated set thereof that is compatible with each selected option;
provide an interface field for each respective component record, said interface fields being arranged to hold data relative to an interface of the component to which the respective component record relates; and
generate a list of compatible component records from at least one logical unit table other than the logical unit table containing said identified specific component record, said compatible records being compatible with said identified specific component record taking account of the data held in the interface fields of said identified specific component record and the component records in said other logical unit table.

34. The article of manufacture of claim 33, wherein each option of the option lists comprises a further set of specific component records; and wherein the program code for causing the computer to identify the unique specific component record includes a program code for causing the computer to form the intersection of the further specific component records of the selected options and the associated set of specific component records.

35. The computer program of claim 33, wherein the program code further causes the computer to make at least one of said option lists available to the user for selection therefrom in at least two of said generic component records.

36. The article of manufacture of claim 33, wherein each one of a plurality of said component records is a generic component record relating to a respective generic component.

37. The article of manufacture of claim 36, further comprising program code for causing the computer to provide for each of said generic component records a respective associated set of specific component records and at least two option lists.

38. The article of manufacture of claim 33, wherein at least one of said compatible component record is a further generic component record relating to a further generic component, and wherein the program code further causes the computer to:

provide for said at least one further generic component record an associated set of further specific component records and at least two option lists, each of which option lists relates to a defined characteristic of the component of the associated further generic component record;

allow the user to select an option from each option list associated with the further generic component record; and identify a unique further specific component record from said further associated set thereof that is compatible with each option selected from the option lists associated with the further generic component record.

* * * * *